(12) United States Patent
Kenison et al.

(10) Patent No.: US 6,953,586 B1
(45) Date of Patent: Oct. 11, 2005

(54) GROWTH PROMOTING PHARMACEUTICAL IMPLANT

(75) Inventors: Dale C. Kenison, Overland Park, KS (US); William G. Zollers, Jr., Grandview, MO (US)

(73) Assignee: Ivy Animal Health, Inc., Overland Park, KS (US)

( * ) Notice: Subject to any disclaimer, the term of this patent is extended or adjusted under 35 U.S.C. 154(b) by 0 days.

(21) Appl. No.: 09/589,730

(22) Filed: Jun. 8, 2000

(51) Int. Cl.[7] .............................................. A61K 9/14
(52) U.S. Cl. ..................... 424/422; 424/426; 424/468; 424/489; 514/178; 514/182; 604/891.1
(58) Field of Search ............................... 514/182, 178, 514/30–32; 424/433, 458–462, 468–472, 424/422, 426, 438, 484–488, 408; 604/891.1

(56) References Cited

U.S. PATENT DOCUMENTS

| | | |
|---|---|---|
| 3,939,265 A | 2/1976 | Grandadam |
| 4,192,870 A | 3/1980 | Grandadam et al. |
| 4,670,249 A * | 6/1987 | Ivy et al. ................... 424/424 |
| 4,799,921 A | 1/1989 | Johnson et al. ............... 604/51 |
| 4,847,243 A | 7/1989 | Wallace |
| 4,994,227 A | 2/1991 | Dietz et al. |
| 5,035,891 A * | 7/1991 | Runkel et al. .............. 424/423 |
| 5,098,425 A | 3/1992 | Eckenhoff |
| 5,200,196 A | 4/1993 | Ayer et al. |
| 5,204,116 A | 4/1993 | Edgren et al. |
| 5,378,474 A | 1/1995 | Morella et al. |
| 5,416,073 A | 5/1995 | Coy et al. |
| 5,453,418 A | 9/1995 | Anderson et al. |
| 5,609,884 A | 3/1997 | Desai |
| 5,686,413 A | 11/1997 | Anderson et al. |
| 5,731,001 A * | 3/1998 | Magruder et al. .......... 424/473 |
| 5,874,098 A * | 2/1999 | Stevens et al. ............. 424/408 |
| 5,874,418 A | 2/1999 | Stella et al. |
| 5,980,508 A * | 11/1999 | Cardamone et al. ..... 604/890.1 |

FOREIGN PATENT DOCUMENTS

| | | |
|---|---|---|
| EP | 89302096.6 | 2/1989 |
| WO | WO99/15166 | 4/1999 |
| WO | WO99/51201 | 10/1999 |
| WO | 00/25743 | * 5/2000 |

OTHER PUBLICATIONS

Ensminger-Stockman's Handbook pp 225-226, 78.*
Samber etal Implant-J.Amin.Sci. 74(7) pp 1470-1476, '96.*
Johnson etal J.Amin.Science 76(2) 491-497, '98.*

* cited by examiner

*Primary Examiner*—Neil S. Levy
(74) *Attorney, Agent, or Firm*—Sonnenschein Nath & Rosenthal LLP

(57) ABSTRACT

A combination growth promoting pharmaceutical pellet system which delivers doses of both a growth stimulating pharmaceutical agent and a supplemental agent that enhances the growth produced by the growth stimulating agent as part of a single procedure wherein the doses have a synergistic or augmentative effect on physiological growth and weight gain. The system includes an implanter apparatus for subcutaneously implanting pellets in an animal through the bore of a hypodermic needle which is operably coupled to a pellet magazine, and a plurality of pellets sized to be implanted through the needle and positioned in the magazine for selective alignment of a pellet with the needle. The pellets include at least one growth stimulating pharmaceutical agent dose pellet. The implant also includes a supplemental agent dose selected from the group of parasiticides, antibiotics, estrus suppressing compositions, somatotropins, gonadotropins and mixtures thereof. The various agents preferably include both immediate release and time delayed release components.

5 Claims, 1 Drawing Sheet

GROWTH PROMOTING PHARMACEUTICAL IMPLANT

BACKGROUND OF THE INVENTION

The present invention is broadly concerned with a pellet implant system that administers a growth stimulating pharmaceutical pellet dosage in combination with a parasiticidal, antimicrobial, estrus suppressant and/or other supplemental pellet dosage subcutaneously in a single procedure in order to promote physiological growth which is synergistically augmented and promoted by control of parasites, microbes and/or estrus and the like.

More particularly, it is concerned with an implantation device having a pellet magazine containing pellets having a growth stimulating pharmaceutical in combination with a parasiticide, an antimicrobial agent and/or an estrus suppressant or other supplemental agent in a growth promoting combination as well as an injection needle and structure permitting injection of the pellets from the magazine through the needle for implantation under the skin of an animal. The pellets are formulated to simultaneously deliver doses of the various components that are released in the body of the animal according to a predetermined schedule.

Subcutaneous implantation of pharmaceutical compositions and medical devices has been widely adopted for therapeutic, health and growth enhancement purposes for livestock and companion animals, humans and even certain wild animals, such as those maintained in parks and zoos. Various growth promotants are employed to foster improved growth and enhanced body weight in livestock animal species such as cattle, swine, sheep, poultry and the like.

Broad spectrum endectocides, that is, pharmaceutical compositions which control both internal and external parasites, are now available to control the numerous members of the Arthropoda and Nematoda phyla, such as flies, mosquitoes, midges, keds, lice, maggots, mites, ticks, and their larvae, worms, wasps, and predaceous beetles and have been applied to animals in various ways. Antimicrobials have been employed for prophylactic as well as acute treatment of respiratory and other bacterial diseases. Estrus suppressors are used to maintain appetite and enhance growth, especially in cattle.

These compounds have been employed for various purposes to effect the health of animal populations, as well as production, performance and reproductive efficiency. Some of these compounds also relieve discomfort which may accompany pest infestation and infection. Other types of biologically active compounds, including vitamins, anti-inflammatory agents, vaccines and biocides are also commonly used to improve the health status of animal populations.

Some of these compositions are implantable in animals, such implantable compositions are often administered as solid compressed pellets which are injected by an implanter equipped with a hypodermic needle. In livestock implants are normally made in the ear or in other areas of the animal that are not for consumption and are discarded. The implanter needle is used to make a small self-sealing and noncoring implant-receiving puncture beneath the skin at a suitable location on the body of the animal. Small pellets of a bioactive composition are forced through the needle and left under the skin as the needle is removed.

The pellets are normally implanted in non-poultry livestock animals while the animal is confined in a squeeze chute. Using head restraint, an ear is grasped in one hand, and an implanter device having a large hypodermic needle is used to puncture the hide and subcutaneously inject a pellet dose into an implant-receiving puncture. Implantation must be performed carefully to ensure that the pellets are placed properly and that no portion of the pellet remains extending from the puncture outside the hide. The procedure must also be performed quickly, since the animals are not entirely cooperative and may shake their heads to free the held ear.

U.S. Pat. No. 5,522,797 and entitled Slide Action Veterinary Implanter, is directed to an implanter of the type described above and is hereby incorporated by reference. This patent discloses an implanter which employs a slide action mechanism to retract an impeller, store an impeller driving force in a spring in cooperation with a latch mechanism, reset a trigger, and advance a pellet magazine, all by a single trigger actuated reciprocation of the slide mechanism. Operation of the trigger also forces the pellets from the magazine through the needle and under the skin of the animal.

Efficient implanters, such as that taught in the above noted patent and other patents to similar implanters, permit rapid sequential injection of many animals in a single session and make implant technology particularly well-suited for administration of bioactive compositions, while the animals are confined for ear tagging, branding, veterinary procedures or the like. Even where only a single animal is to be treated, implantation offers a particularly safe method for administering certain compositions, so as to allow a user to avoid compounds that could be toxic if ingested by the animal, for example by licking residue left on the hide or fur, or on that of another animal following treatment by dipping, spraying or dusting.

Physiological growth and weight gain in particular are of primary importance in livestock animals raised for meat. Parasite control has long been a primary goal of animal husbandry. A number of effective endectocides and insect growth regulators are available for control of arthropod and nematode parasites, including the polyketide avermectins, the milbemycins and milbemycin oximes, fenbendazole, pyriproxyfen and lufenuron, diflubenzuron, methoprene, ethyl carbamate and fenoxycarbu. The most commonly used avermectins are ivermectin, doramectin, moxidectin, eprinomectin and abamectin. U.S. patent application Ser. No. 09/163,646, now U.S. Pat. No. 6,645,192 for Pellet Implant System for Immediate and delayed Release of Antiparasitic Drug, which is incorporated herein by reference, discloses a system which delivers subcutaneously pellet implants of varying controlled release parasiticidal dosages to provide immediate as well as sustained release of the parasiticide for a period of up to several months without redosing.

Respiratory disease and its consequent growth impairment is a particular problem among crowded animals, such as is found in feedlots. Suitable antimicrobial compositions include tylosin tartrate, tylosin, oxytetracycline, tilmicosin phosphate, ceftiofur hydrochloride, ceftiofur sodium, and sulfadimethoxine. Prophylactic administration of these antibiotics permits usage of lower doses than those required to treat an infected animal.

Similarly, estrus-induced appetite inhibition in food animals diminishes weight gain. Effective growth promoting pharmaceutical compositions are available, including the progestins, estradiol and its derivatives, trenbolone acetate, testosterone and zeranol. Somatotropins and gonadotropins are also used for various purposes in livestock.

It has been noted in accordance with the present invention that administration of a growth stimulating composition in association with effective control of internal and external parasites results in a highly effective growth promoting composition and an augmentation of the physiological growth of the animal. In certain circumstances, the animals may even gain significantly more weight than is predicted from summation of the predicted effects of the individual compounds, as there is a synergistic effect associated with combining the various compositions and implanting them together. Accordingly, there is a need for a system which delivers subcutaneously pellet implants of both a growth stimulating pharmaceutical dosage in combination with a parasiticidal dosage, an antimicrobial dosage, an estrus suppressant dosage and/or other supplemental agents to provide control of parasites, microbial infection, estrus and maximize promotion of growth.

SUMMARY OF THE INVENTION

The present invention provides a greatly improved pharmaceutical implant system which simultaneously delivers separate doses of both a growth stimulating pharmaceutical agent and a second component chosen from a group including parasiticides, antibiotics, estrus suppressors somatotropins and/or gonadotropins into an animal as part of a single procedure wherein the doses preferably have a synergistic augmentative effect on physiological growth and weight gain.

Broadly speaking, the implant system includes an implanter apparatus for subcutaneously implanting growth promoting pharmaceutical solid implants, especially in the form of pellets, into an animal through the bore of a hypodermic needle which is operably coupled with a pellet magazine, and one or a plurality of pellets sized to be implanted through the needle and positioned in the magazine for selective sequential alignment of the implant with the needle.

The pellets include at least one growth stimulating pharmaceutical agent dose and at least one supplemental agent dose, especially chosen from the group comprising parasiticides, antibiotics and estrus suppressors, as well as other supplemental agents. Each of the pellets may include a single component or the pellets may each contain a mixture of two or more of the agents. A complete set of the pellets is packaged in a stack in the magazine in an individual dosing chamber for simultaneously delivery of the supplemental agents and the growth stimulating pharmaceutical as part of a single injection.

Advantageously, the system permits the pellet doses to be formulated for both immediate and controlled, sustained release of an effective dose of the growth stimulating pharmaceutical agent and each of the supplemental agents. The immediate and sustained release doses may be the same or different growth stimulating and supplemental agents, with the principal difference being that different pellet excipients are employed to reduce or lengthen the dose delivery period. Preferably, the delivery rates of the doses are correlated so that combined doses of each of the growth stimulating agent and the supplemental agent are delivered simultaneously both immediately and over a sustained release period of time to produce a highly efficacious, synergistic and long lasting growth promoting combination.

OBJECTS AND ADVANTAGES OF THE INVENTION

Therefore, the principal objects and advantages of the present invention are: to provide an animal growth promoting composition having in combination a growth stimulating pharmaceutical agent and at least one supplemental agent selected from parasiticides, antimicrobials, estrus suppressing compositions, somatotropins, gonadotropins and other agents that enhance the effect of the growth stimulating agents; to provide such a composition having a pellet system for the implantation in an animal; to provide such a composition having immediate as well as sustained delivery of both a growth stimulating pharmaceutical agent and at least one supplemental agent in order to synergistically promote physiological growth of an animal; to provide such a system which includes an implanter apparatus for subcutaneously injecting pellets in an animal through the bore of a hypodermic needle which is operably coupled with a pellet magazine and simultaneously introduces both growth stimulating pharmaceutical and supplemental agent doses that are contained in separate or common pellets; to provide such a system and method which permits injection of predetermined doses in a solid bio-erodible and subsequent system absorbable form of each of a growth stimulating pharmaceutical and a supplemental agent in a single injection; to provide such a system and method which permits subcutaneous injection of both the growth stimulating pharmaceutical dose and the supplemental agent dose; to provide such a system and method which permits serial injection of large numbers of animals in a single session; to provide such a system and method which may employ a wide range of growth stimulating pharmaceutical agents for use in growth promotion; to provide such a system and method which is simple and efficient and economical to manufacture, which effectively promotes enhanced growth of the animal and which is particularly well-adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
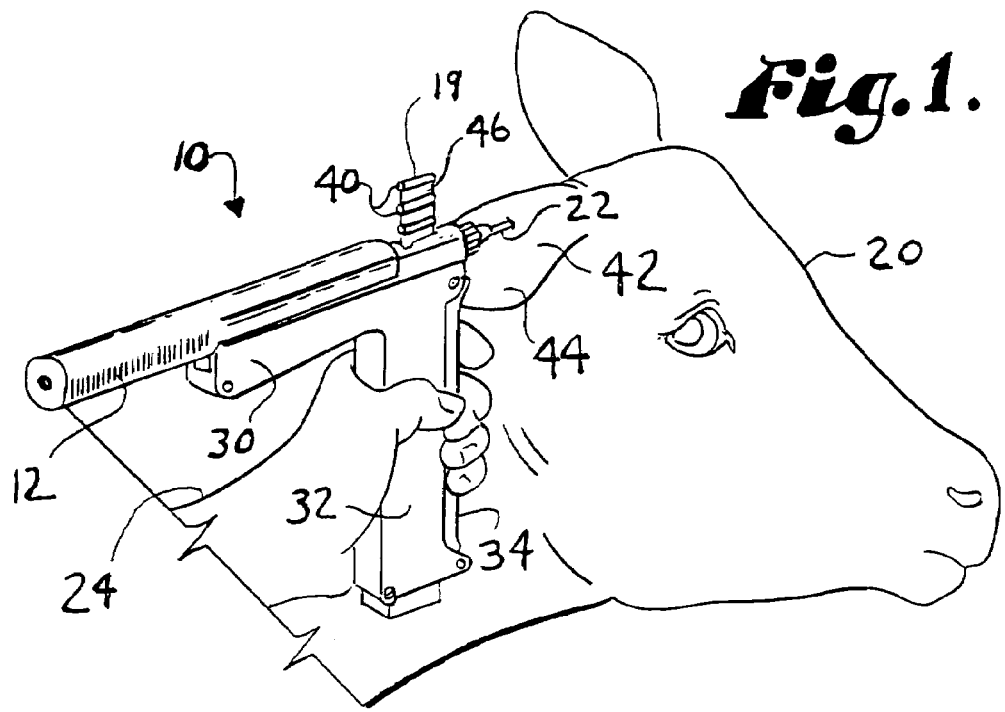
FIG. 1 is a fragmentary perspective view of a cow, an implanter apparatus with implants in accordance with the present invention and an apparatus operator.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 10 represents a pellet implantation system in accordance with the invention. The implantation system 10 broadly includes a slide action implanter apparatus 12 which is used to implant solid form bioactive compounds or implants 13 having various formulations in accordance with the invention, including a growth stimulating pharmaceutical agent compressed in a first pellet 14, a parasiticidal agent compressed in a second pellet 15, an immediate release antimicrobial agent in a third pellet 16, a delayed release antimicrobial agent in a fourth pellet 17 and an estrus suppressing agent in a fifth pellet 18. The pellets 14 through 18 are included in stacks in a magazine strip 19 and injected into an animal 20 through a hypodermic needle 22. The needle 22 is utilized by an operator 24 to create a hide opening 26 that produces an implant-receiving puncture 28 in the animal 20.

Different types of implanters may be used with the invention and a suitable implanter apparatus is illustrated and described in detail in the U.S. Pat. No. 5,522,797 patent. The implanter apparatus 12 generally includes a housing 30 having a finger grip 32 with a trigger assembly 34 pivotally mounted therein. An impeller 36 is slidably mounted within the housing 30 in alignment with an interior bore 38 of the needle 22 and aligned chambers 40 of the loaded pellet magazine strip 19. The needle 22 is used to puncture through skin or hide 42 of an animal's ear 44 at the opening 26, and the trigger 34 is squeezed toward the grip 32 of the housing 30 to initiate injection of the pellets 14 through 18 by urging the impeller 36 through the magazine chamber 40 and needle bore 38, thereby forcing the pellets 14 to 18 through the bore 38 of needle 22 and into the puncture 28 in the ear 44.

Each magazine strip 19 of the implanter 12 typically contains multiple parallel aligned implants 13 that contain stacks of pellets stored in corresponding pellet chambers 40, which are interconnected by webs 46. The chambers 40 are slightly conical in shape and are arranged in side-by-side parallel relation. The chambers 40 may have internal frictional formations such as beads or posts (not shown) to retain the pellets 14 through 18 therein prior to insertion and such beads can be easily overcome and bypassed by application of pressure to the trigger 34. A plurality of strips 19 can be connected in end-to-end relation to increase the implanting capacity before the implanter 12 requires reloading. When the pellets 14 through 18 in an individual magazine strip 19 are exhausted, the empty strip 19 can be detached from the remaining strips 19 located in the implanter 12 and discarded.

In the present embodiment, each pellet chamber 40 is loaded with one or more growth stimulating pharmaceutical agent dose pellet 14 and one or more supplemental agent pellet, here pellets 15 to 18. The pellets 14 through 18 each include an effective amount of one or more of the agents, formed into a compressed pellet in conjunction with one or more excipients so as to form either an immediate or a delayed release pellet.

In accordance with the invention the pellets 14 to 18 include at least one growth stimulating agent and at least one supplemental agent that cooperatively works with the growth stimulating agent to promote growth in the animal, as a growth promoting combination. The supplemental agent is preferably a combination of an immediate release and quick acting parasiticide to immediately rid the animal of infestation by pests and a long term release and delayed acting parasiticide to maintain the animal free of infestation of pests over a substantial period of time, both immediate release and long term release antibiotics to keep the animal free of microbial infection and an estrus suppressing composition to keep the animal from entering estrus.

In accordance with the invention it is possible that one or more growth stimulating agents and one or more supplemental agents could be mixed together and incorporated in a single pellet; however, because each of the agents may be absorbed at different rates or require different carriers, normally there will be a different pellet, such as pellets 14 through 18 for each of the agents. Therefore, while it is seen to be preferable to have individual pellets for each of the different agents, it is well within the scope of the invention to have a single elongate or multiple shorter pellets with mixtures of two or more agents or to have some agents in separate pellets injected with other agents that are mixed and formed into a common pellet.

A wide range of active ingredients may be employed as growth stimulating pharmaceutical agents, for example the progesterone, estradiol and derivatives thereof including estradiol benzoate, trenbolone acetate, testosterone propionate and zeranol. As used herein, the term growth stimulating pharmaceutical agent is intended to include such agents as noted above and other compositions that operably function under the present invention to promote physiological growth and which may be used internally in the particular species of animal to be treated by the invention.

A wide range of active ingredients may be employed as parasiticidal agents, for example, the polyketide avermectins, such as ivermectin, doramectin, moxidectin, eprinomectin and abamectin, the milbemycins and milbemycin oximes, fenbendazole, oxfendazole and lufenuron. As used herein the term parasiticide is intended to include parasiticides as noted above and other compositions that operably function under the present invention as parasiticides in combating infestation and preventing reinfestation by internal and external parasites and which may be used internally in the particular species of animal to be treated by the invention.

It is noted that the amount of growth stimulating pharmaceutical agent or supplemental agent required to produce the desired treatment varies with respect to the species and size of the animal to be treated.

For example, in pasture cattle the growth stimulating agent may be estradiol benzoate in a range from 5 to 50 milligrams per implant, preferably within the range of 10 to 30 milligrams and most preferred with a dosage of 20 milligrams. For pasture or feedlot heifers the growth stimulating agent may be trenbolone acetate in a range of 20 to 400 milligrams per implant, preferably in a range of 40 to 100 milligrams for pasture heifers and 150 to 250 milligrams for feedlot heifers. For the cattle entering a feed yard the growth stimulating agent may be estradiol in a range from 5 to 50 milligrams per implant, with a preferred range of 15 to 30 milligrams and a most preferred dosage of 25 milligrams.

Further for example, when treating cattle, an immediate release parasiticidal pellet for control of insects, arachnids, especially ticks and nematodes, preferably contains between about 25 and 125 milligrams of ivermectin and the sustained released combined parasiticidal pellets contain between about 50 and 175 milligrams of ivermectin. Parasiticidal agents having extended circulatory half-lives, such as ivermectin, are particularly preferred. A parasiticide pellet formulation may include ivermectin in a range from 100 to 500, preferably in the range from 200 to 400 milligrams and most preferably in a dosage of 300 milligrams per implant.

The estrus suppressing compositions or agents include melengestrol acetate, norgestomet and other progestins. When melengestrol acetate is used as the estrus suppressing agent in cattle, the normal range of dosage is 10 to 100 milligrams per implant with a preferred range of 20 to 80 milligrams and with a most preferred dosage of 60 milligrams.

Suitable antibiotic or antimicrobial agents for many animals include tylosin tartrate, tylosin, oxytetracycline, tilmicosin phosphate, ceftiofur hydrochloride, ceftiofur sodium and sulfadimethoxine. For example, when tilmicosin phosphate is utilized as the antibiotic agent for cattle, typical dosage would normally be in the range from 500 to 1500 milligrams per implant with a preferred range of 750 to 1250 milligrams and a most preferred dosage of 1000 milligrams. It is foreseen that various mixtures of agents both in general and within a specific class can be used in accordance with the invention.

The pellets are formulated so as to be biodegradable or bio-erodible in the target animal and to control release of the growth stimulating agent and each of the supplemental agents at complementary different rates and so that the animal also preferably receives both immediate and extended release doses of each of the agents. Pellets formulated for extended release combine an effective dose of a supplemental agent such as the parasiticide ivermectin or a growth stimulating pharmaceutical agent such as progesterone with binding agent excipients that lengthen the implant delivery period by extending the integrity of the pellet and limiting the hydration of the pellet by extracellular fluid entry into the pellet. In this manner, the extended pharmacokinetics of the agent, delayed bio-erosion of the pellet, and delayed diffusion of the agent dose into the animal's circulatory system cooperatively result in an extended release dosage which makes available for absorption an effective dose of the agent over a period of months, for example 150 days.

Any of a number of excipients may be employed in the extended release pellets, including lactose, polyethylene glycol, as sold under the trademark Carbowax® by Union Carbide, cholesterol magnesium stearate, cellulose and its derivatives, especially ethylcellulose as sold under the trademark Ethocel® by Dow, povidone, crospovidone, croscarmellose, dicalcium phosphate, polymeric supports, binders and coloring agents.

The immediate release pellets make the agent available for absorption into the bloodstream of the animal immediately (normally within hours or a few days) and may include the previously listed excipients as well as disintegration aids such as magnesium stearate and croscarmellose sodium, especially as sold under the trademark Ac-Di-Sol® by FMC and microcrystalline cellulose, especially as sold under the trademark Avicell® by FMC.

Each immediate release pellet is formulated to dissolve and enter the animal's blood system (systemically) within a few days, preferably within hours of injection. The extended release pellets are formulated to release active agent into the animal's blood system slowly and continuously over a period of many days, for example about 150 days, in order to sustain a sufficient level of the agent systemically in the animal being treated to effect the desired result of the agent.

The compressed pellets 14 through 18 can be produced inexpensively and in large quantities by a variety of conventional manufacturing equipment.

In the illustrated embodiment, a first pellet 14 has a growth stimulating pharmaceutical agent dose of estradiol benzoate, a second pellet 15 includes an immediate release dosage of the parasiticide ivermectin, a third pellet 16 includes a delayed release dosage of the parasiticide ivermectin, a fourth pellet 17 includes an estrus suppressing dosage of melengestrol acetate and a fifth pellet 18 has an antimicrobial dosage of tilmicosin phosphate, although it is foreseen that other combinations including fewer or more agents are possible within the scope of the invention. It is foreseen that the number of pellets within an individual dosing chamber 40 within a magazine 19 for each release formulation within may vary, depending on the desired dose of growth promoting agent and parasiticide to be delivered. As an example, the pellets 14 through 18 may in some instances be combined as a single pellet or may have many pellets.

Each magazine chamber 40 is prefilled with a preferred number of discrete pellets 14 through 18, each containing respectively a growth stimulating pharmaceutical agent and/ or a supplemental agent dose in a compressed pellet formulation which may be designed for immediate or extended release or a combination thereof, the chamber 40 has at least one pellet 14 including a growth stimulating pharmaceutical agent dose and one or more pellets 14 through 18 including one or more supplemental agents.

Figure 2:
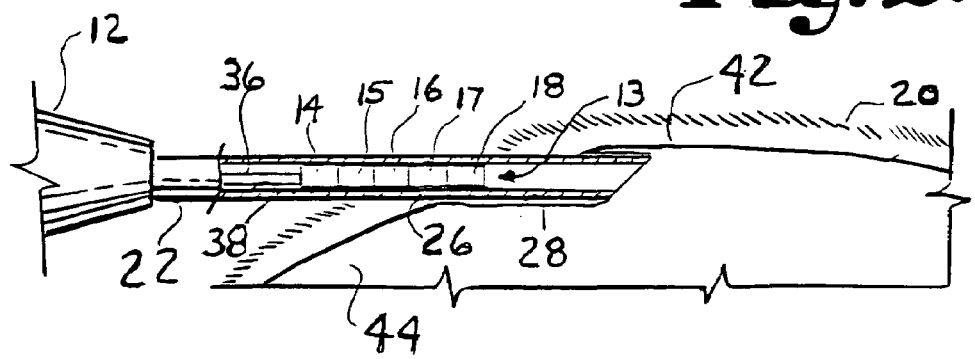
FIG. 2 is an enlarged, fragmentary side elevational view of the cow and implanter apparatus illustrating a hypodermic needle of the implanter with implant pellets inside the needle being inserted into an ear of the cow, with portions broken away to show working detail.
Figure 3:
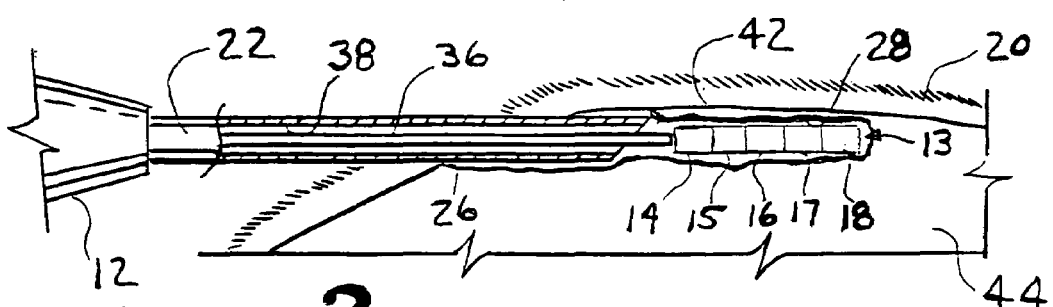
FIG. 3 is an enlarged, fragmentary side elevational view of the cow and implanter apparatus similar to FIG. 2, illustrating subcutaneous placement of a stack of pellets by the implanter into the ear of the cow, with portions broken away to show working detail.

In use, an operator grasps the implanter 12 by the grip 32 and urges the needle 22 into the hide 42 and under the skin of the target animal 20 to make the implant receiving puncture 28. The puncture 28 shown in FIG. 2, is approximately half complete and is complete in FIG. 3. The operator 24 depresses the trigger member 34, thereby propelling a pin 48 of the impeller member 36 forwardly through an aligned magazine chamber 40, forcing the pellets 14 through 18 through the needle bore 38 and into the implant receiving puncture 28. The operator 24 then withdraws the needle 22, leaving the pellets 14 through 18 in the implant receiving puncture 28.

Where immediate and delayed release agents are utilized the bioerodible excipient and disintegration aids included in the formulation of the immediate release agents make those agents immediately available for systemic absorption an effective dose of the agent or agents typically for up to 30 days. The binders included in the extended release pellets cause delayed bioerosion of the pellets and diffusion of the effective dose of the agents therein for absorption into the bloodstream of the animal over an additional period of up to 120 days. This multicomponent formulation lengthens the pellet delivery period for the agent doses so that effective blood levels of the agents are maintained for periods of up to about 150 days.

Advantageously, the magazine strip 19 may be loaded for selective injection of any number of growth stimulating pharmaceutical pellets 14 or immediate release or extended release supplemental agent pellets, such as pellets 15 to 18 in order to obtain delivery of a selected dosage by each formulation of agent tailored to the species, weight, age or sex in a wide variety of animals. Where a number of pellets of each formulation of pellets of a single or multiple agent are to be delivered, the pellets may be alternated. In other embodiments, the pellets 14 through 18 may be alternated or varied with respect to the incorporated agents in a stack of pellets of other pharmaceuticals, for delivery through the implant receiving puncture 28.

The pellet system 10 of the present invention may be employed efficaciously with cows, sheep, swine, goats, poultry, horses, dogs, cats or any other suitable animal, including wild animals and humans.

The following example is provided for the purpose of illustrating the invention and is not intended to be limiting upon the scope of the claims.

EXAMPLE I

An implant is produced of multiple pellets sized, shaped and numbered to fit as a stack in a single bore of a pellet magazine of an implanter. The pellets include six discrete pellets including a total of 20 milligrams of estradiol benzoate alternated with pellets including a total of 300 milligrams of ivermectin. One of the implants is placed subcutaneously in each pastured cow to be treated beneath the hide of the ear and the process is repeated every 150 days.

EXAMPLE II

An implant is produced of multiple pellets sized, shaped and numbered to fit as a stack in a single bore of a pellet magazine of an implanter. The pellets include certain pellets having a total dose of 200 milligrams of trenbolone acetate and others having a total dose of 60 milligrams of melengestrol acetate. The implant is injected beneath the skin of the ear of a feedlot heifer.

EXAMPLE III

A solid implant is produced containing a composition in a pellet form sized and shaped to fit a single bore of a magazine of a pellet implanter. The pellet composition comprises a total of 25 milligrams of estradiol and 1000 milligrams of tilmicosin phosphate. The implant is injected under the hide of the ear of a feed yard cow for promotion of growth coupled with and augmented by prophylactic treatment for respiratory disease.

As used herein the term supplemental agent is an agent that cooperates with the growth stimulating agent to provide greater physical growth in the animal receiving an implant with both a growth stimulating agent and the supplemental agent than would be expected from just the growth stimulating agent.

Also as used herein the term bio-effective derivative means a composition that performs the same type of function as the composition from which it is derived in a target animal without being harmful to the animal.

It is to be understood that while certain forms of the present invention have been illustrated and described herein, it is not to be limited to the specific forms or arrangement of parts described and shown.

What is claimed and desired to be secured by Letters Patent is as follows:

1. A bio-absorbable and bio-compatible implant for placement under the skin of an animal comprising:
    at least one discrete, solid pellet having a growth promoting agent comprising from about 20–200 mg trenbolone acetate;
    at least one discrete, solid pellet having a supplemental agent comprising from about 10–100 mg melengesterol acetate;
    wherein said agents combine to promote growth in an animal.
2. The implant according to claim 1 wherein said growth promoting agent further comprises from about 5–50 mg estradiol benzoate.
3. The implant according to claim 1 wherein said growth promoting agent further comprises from about 5–50 mg estradiol.
4. A bio-absorbable and bio-compatible implant for placement under the skin of an animal comprising:
    at least one discrete, solid pellet having a growth promoting agent comprising from about 5–50 mg estradiol benzoate;
    at least one discrete, solid pellet having a supplemental agent comprising from about 10–100 mg melengesterol acetate;
    wherein said agents combine to promote growth in an animal.
5. A bio-absorbable and bio-compatible implant for placement under the skin of an animal comprising:
    at least one discrete, solid pellet having a growth promoting agent comprising from about 5–50 mg estradiol;
    at least one discrete, solid pellet having a supplemental agent comprising from about 10–100 mg melengesterol acetate;
    wherein said agents combine to promote growth in an animal.

* * * * *